United States Patent
Hsieh

[19]

[11] Patent Number: 5,919,516

[45] Date of Patent: Jul. 6, 1999

[54] PROCESS OF MAKING JOSS-STICKS

[76] Inventor: Chen-Hui Hsieh, 8F-6, No. 100, Hoping E. Rd., Sec. 2, Taipei, Taiwan

[21] Appl. No.: 08/984,845

[22] Filed: Dec. 4, 1997

[51] Int. Cl.[6] .................................. B05D 1/18; B05D 1/36
[52] U.S. Cl. .......................... 427/180; 427/202; 427/203; 427/430.1
[58] Field of Search .................................. 427/180, 201, 427/430.1, 372.2, 202, 203

[56] References Cited

U.S. PATENT DOCUMENTS

| 4,158,549 | 6/1979 | Martin | 44/1 K |
| 5,618,548 | 4/1997 | Dawson | 424/405 |

FOREIGN PATENT DOCUMENTS

| 59-16815 | 1/1984 | Japan . |
| 7-309736 | 11/1995 | Japan . |

*Primary Examiner*—Frederick Parker
*Attorney, Agent, or Firm*—Rosenberg, Klein & Bilker

[57] ABSTRACT

A process of making environmentally friendly joss-sticks including grinding high-grade carbon materials into powder and mixing the carbon powder with a gum producing powder at a suitable proportion to form a gum-carbon powder mixture; adding a suitable amount of incense to the gum-carbon powder mixture; soaking the bamboo sticks in water and dipping them in the gum producing powder; and soaking the bamboo sticks in water again and dipping them in the gum-carbon powder mixture. The bamboo sticks may further be soaked in water and dipped in a powdered pigment after being wrapped by the gum-carbon powder mixture.

2 Claims, 2 Drawing Sheets

PROCESS OF MAKING JOSS-STICKS

BACKGROUND OF THE INVENTION (a) Field of the Invention

The present invention relates generally to a process of making joss-sticks, and more particularly to a process of making joss-sticks that are environmental friendly and colored, yet without the use of dyes.

(b) Description of the Prior Art

Conventional joss-sticks are made of wood materials such as ebony and they often produce a lot of black smoke and tar during burning as a result of the water moisture and oil contents in the wood, which is harmful to health and the environment. For colored joss-sticks, dyes are required. The use of dyes may also create environmental pollution. Besides, the process of dyeing is time-consuming and therefore increases costs.

SUMMARY OF THE INVENTION

A primary object of the present invention is to provide a process of making environmental-friendly joss-sticks which do not produce much black smoke or tar during burning and which are economical to make. The process comprises grinding high-grade carbon materials into powder and mixing the carbon powder with a gum producing powder in a suitable proportion to form a gum-carbon powder mixture; adding a suitable amount of incense to the gum-carbon powder mixture; soaking the bamboo sticks in water and dipping them in the gum producing powder; and soaking the bamboo sticks in water again and dipping them in the gum-carbon powder mixture. The bamboo sticks are then dried.

Another object of the present invention is to provide a process of making colored joss-sticks without the use of dyes so as to avoid environmental pollution. The joss-sticks are dipped in a gum-pigment powder mixture after covering with a layer of the gum-carbon powder mixture so that they have an inner layer of carbon material and an outer layer of pigment.

BRIEF DESCRIPTION OF THE DRAWINGS

The foregoing and other features and advantages of the present invention will be more clearly understood from the following detailed description and the accompanying drawings, in which.

DETAILED DESCRIPTION OF THE PREFERRED EMBODIMENT

Figure 1:
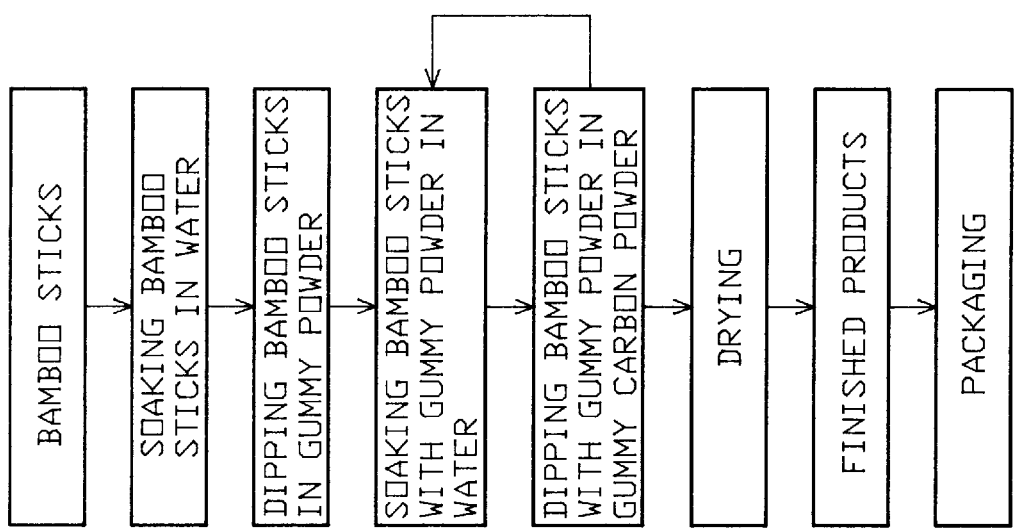
FIG. 1 is a flow-chart of a preferred embodiment of the process according to the present invention.

With reference to FIG. 1, which shows a first preferred embodiment of the present invention, the process of making joss-sticks according to the present invention comprises the following steps of:

1. preparing carbon materials, which may be charcoal, activated carbon, smokeless charcoal, etc.;
2. selecting high-grade carbon from the carbon materials and, if the selected carbon materials fall short of being high-grade, baking the selected carbon materials to remove all residual moisture and oil contents therein;
3. grinding the carbon materials into fine carbon powder;
4. grinding a gum producing material into fine powder to make a gum producing powder, and mixing a portion of the gum producing powder with a portion the carbon material powder in suitable proportions to form a gum-carbon powder mixture, to which is added a suitable amount of incense;
5. soaking bamboo sticks in water and dipping them in the gum producing powder, then dipping them in the gum-carbon powder mixture for a suitable number of times depending on the required thickness of the joss-sticks so as to obtain joss-sticks with carbon materials; and
6. drying the joss-sticks and packaging them. In step 5, the step of dipping the bamboo sticks in the gum-carbon powder mixture can be carried out by hand or conventional joss-stick making machines.

Figure 2:
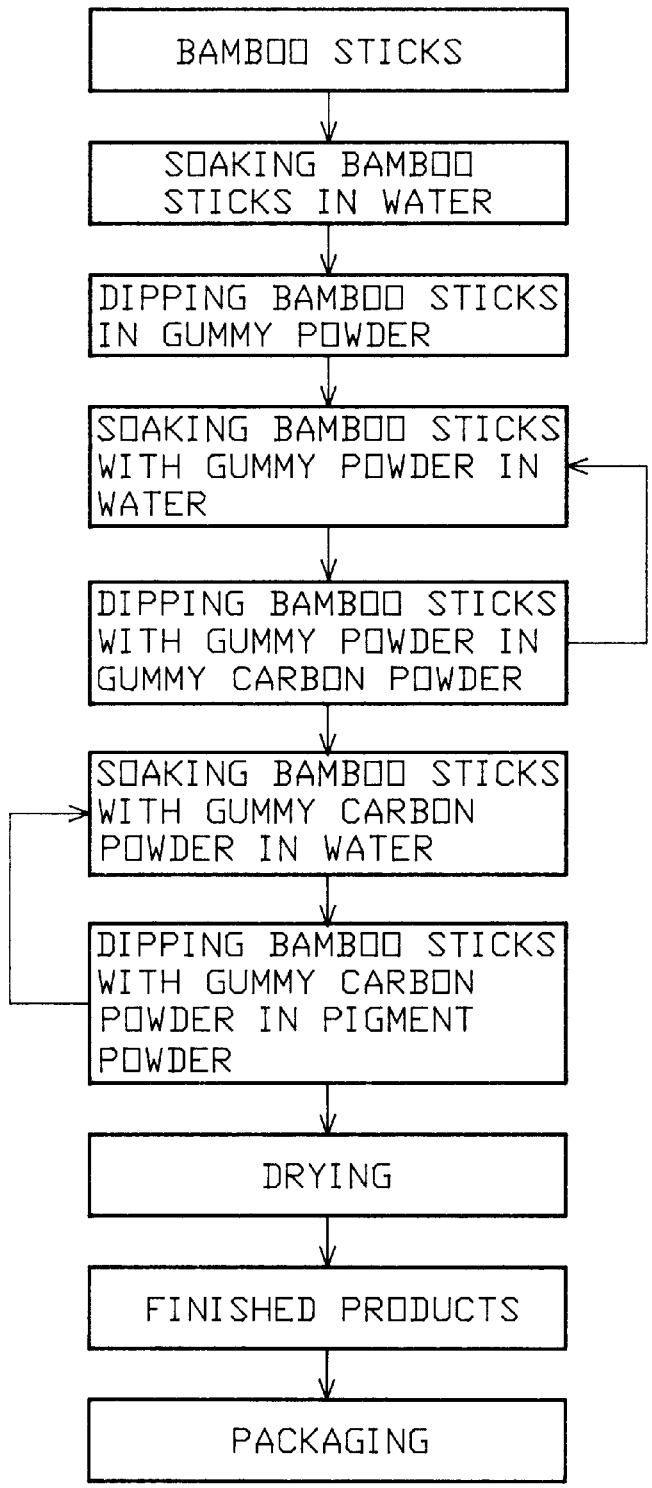
FIG. 2 is a flow-chart of another preferred embodiment of the process according to the present invention.

Referring to FIG. 2, which shows a second preferred embodiment of the present invention, the present invention may further comprise a step of grinding pigment materials into a fine powder and mixing it with the gum producing powder in a suitable proportion to form a colored gum producing powder. After the bamboo sticks are soaked in water and wrapped by a suitable amount of gum-carbon powder mixture, the bamboo sticks are further soaked in water and then dipped in the colored gum producing powder for a suitable number of times so that the joss-sticks thus formed have an inner layer of carbon materials and an outer layer of pigment materials.

When burned, as the joss-sticks of the present invention do not produce much smoke or tar, they are environmentally friendly. Besides, since the joss-sticks of the invention do not require the step of dyeing, the manufacturing cost is reduced. The elimination of the use of dyes also helps to reduce environmental pollution.

Although the present invention has been illustrated and described with reference to the preferred embodiment thereof, it should be understood that it is in no way limited to the details of such embodiment but is capable of numerous modifications within the scope of the appended claims.

What is claimed is:

1. A process for making joss-sticks, comprising the steps of:
   a. providing a carbon material, said carbon material being devoid of residual moisture and oil;
   b. grinding said carbon material into a carbon powder;
   c. providing a gum producing material;
   d. grinding said gum producing material into a powder;
   e. mixing said carbon powder with said gum producing powder in a predetermined proportion to form a gum-carbon mixture;
   f. mixing an incense with said gum-carbon mixture;
   g. soaking bamboo sticks in water;
   h. dipping the bamboo sticks into said gum producing powder for adhering said gum producing powder to the bamboo sticks;
   i. coating said dipped bamboo sticks with said gum-carbon-incense mixture by further dipping said dipped bamboo sticks into water followed by dipping into said gum-carbon-incense mixture at a least one time to form coated bamboo sticks; and,
   j. drying and packaging said coated bamboo sticks.

2. The process for making joss-sticks as recited in claim 1 where the step of coating includes the steps of:
   a. providing a pigment powder;
   b. mixing said pigment powder with said gum producing powder to form a colored gum producing powder; and,
   c. dipping said coated bamboo sticks in said colored gum producing powder to overlay said coated bamboo sticks with a layer of said colored gum producing powder.

* * * * *